US007157431B2

(12) United States Patent
McAnalley et al.

(10) Patent No.: US 7,157,431 B2
(45) Date of Patent: Jan. 2, 2007

(54) COMPOSITIONS OF PLANT CARBOHYDRATES AS DIETARY SUPPLEMENTS

(75) Inventors: Bill H. McAnalley, Grand Prairie, TX (US); H. Reginald McDaniel, Mansfield, TX (US); D. Eric Moore, Grapevine, TX (US); Eileen P. Vennum, Grand Prairie, TX (US); William C. Fioretti, Grapevine, TX (US)

(73) Assignee: Mannatech, Inc., Coppell, TX (US)

( * ) Notice: Subject to any disclaimer, the term of this patent is extended or adjusted under 35 U.S.C. 154(b) by 0 days.

(21) Appl. No.: 10/797,760

(22) Filed: Mar. 10, 2004

(65) Prior Publication Data

US 2004/0170706 A1 Sep. 2, 2004

Related U.S. Application Data

(63) Continuation of application No. 09/242,215, filed as application No. PCT/US97/13379 on Aug. 4, 1996, now Pat. No. 6,929,807.

(60) Provisional application No. 60/057,017, filed on Jul. 24, 1997, provisional application No. 60/030,317, filed on Nov. 1, 1996, provisional application No. 60/022,467, filed on Aug. 9, 1996.

(51) Int. Cl.
*A01N 43/04* (2006.01)
(52) U.S. Cl. .......................... 514/23; 514/53; 514/54; 514/61; 514/62
(58) Field of Classification Search ............... 424/658, 424/408, 489; 514/22, 23, 53–64, 24
See application file for complete search history.

(56) References Cited

U.S. PATENT DOCUMENTS

| 3,890,438 A | 6/1975 | Cayen et al. |
| 3,947,601 A | 3/1976 | Ortega |
| 4,260,603 A | 4/1981 | Pegel et al. |
| 4,466,958 A | 8/1984 | Morrison |
| 4,593,046 A | 6/1986 | Gruber |
| 4,665,057 A | 5/1987 | Nelson et al. |
| 4,735,935 A | 4/1988 | McAnalley |
| 4,777,045 A | 10/1988 | Vanderveer et al. |
| 4,837,040 A | 6/1989 | Yokoyama et al. |
| 4,851,224 A | 7/1989 | McAnalley |
| 4,855,284 A | 8/1989 | Emoedi |
| 4,859,488 A | 8/1989 | Kan et al. |
| 4,871,557 A | 10/1989 | Linscott |
| 4,917,890 A | 4/1990 | McAnalley |
| 4,957,907 A | 9/1990 | McAnalley |
| 4,959,214 A | 9/1990 | McAnalley |
| 4,966,892 A | 10/1990 | McAnalley |
| 5,021,560 A | 6/1991 | Montreuil et al. |
| 5,106,616 A | 4/1992 | McAnalley et al. |
| 5,118,673 A | 6/1992 | Carpenter et al. |
| 5,202,122 A | 4/1993 | Graves et al. |
| 5,229,118 A | 7/1993 | Campbell |
| 5,284,833 A | 2/1994 | McAnalley et al. |
| 5,292,729 A | 3/1994 | Ashmed |
| 5,294,434 A | 3/1994 | King et al. |
| 5,296,245 A | 3/1994 | Clarke et al. |
| 5,308,618 A | 5/1994 | Konno et al. |
| 5,308,838 A | 5/1994 | McAnalley et al. |
| 5,378,480 A | 1/1995 | Carieri |
| 5,441,943 A | 8/1995 | McAnalley et al. |
| 5,443,830 A | 8/1995 | Moore et al. |
| 5,487,894 A | 1/1996 | Kovacs |
| 5,523,087 A | 6/1996 | Shlyankevich |
| 5,607,693 A | 3/1997 | Bonte et al. |
| 5,612,039 A | 3/1997 | Policappelli et al. |
| 5,710,270 A | 1/1998 | Maeda et al. |
| 5,827,526 A | 10/1998 | Dohnalek et al. |

FOREIGN PATENT DOCUMENTS

| DE | 3935906 | 5/1991 |
| EP | 0052171 | 5/1982 |
| EP | 00561408 A1 | 3/1993 |
| EP | 000561408 A1 * | 9/1993 |
| JP | 57/007420 | 1/1982 |
| JP | 59059624 A | 4/1984 |
| JP | 59/112922 | 6/1984 |
| JP | 63294766 A | 12/1988 |
| JP | 03/255029 | 11/1991 |
| JP | 1995113001 A | 5/1995 |
| JP | 07/242551 | 9/1995 |
| JP | 10279487 A | 10/1998 |
| JP | 10279496 A | 10/1998 |
| NZ | 299607 | 3/1997 |

(Continued)

OTHER PUBLICATIONS

Bradbury, A. G. W. et al., Collaque Scientifique International sur le Café, 1988, 12: 265-269. Polysaccharides in green coffee beans.*
Beldman, G et al. Biotechnology and Bioengineering (1987), 30(5): 668-71. Enzymic hydrolysis of beer brewer's spent grain and the influence of pretreatments.*

(Continued)

*Primary Examiner*—Michele Flood
(74) *Attorney, Agent, or Firm*—Randall C. Brown; Edwin S. Flores

(57) ABSTRACT

Compositions of plant carbohydrates for dietary supplements and nutritional support for promotion and maintenance of good health. Defined nutritionally effective amounts of one to eleven essential saccharides, glyconutrients, are used in various inventive compositions as dietary supplements. The dietary composition herein can include phytonutrients, vitamins, minerals, herbal extracts, and other non-toxic nutrients. The glyconutritional dietary supplement herein provides essential saccharides which are the building blocks of glycoproteins. These compositions, when administered orally or topically, have been found to improve the well being of mammals suffering from a variety of disorders.

9 Claims, No Drawings

FOREIGN PATENT DOCUMENTS

| RU | 2097041 | 11/1997 |
|---|---|---|
| WO | WO 91 15214 | 10/1991 |
| WO | WO 9303727 | 4/1993 |
| WO | WO 9506068 A1 | 3/1995 |
| WO | WO 98/06418 | 2/1998 |

OTHER PUBLICATIONS

Remington, J.S. et al. Industrial Chemist and Chemical Manufacturer (1927), 3:155-7. Breakfast, invalid and infant food.*

Aloe Vera Research—Author unknown, Date of publication, if any, unknown.

Alton, G et al., Direct utilization of mannose for mammalian glycoprotein biosynthesis, Glycobiology, vol. 8, No. 3, 1998, pp. 285-295.

Bond, A et al., Distinct Oligosaccharide Content of Rheumatoid Arthritis-Derived Immune Complexes, Arthritis & Rheumatism, vol. 38, No. 6, 1995, pp. 744-749.

Bond, A et al., The relationship between exposed galactose and N-acetylglucosamine residues on IgG in rheumatoid arthritis (RA), juvenile chronic arthritis (JCA) and Sjögren's syndrome (SS) Clin exp Immunol (1996); vol. 105, pp. 99-103.

Bouic, P et al., Plant Sterols and Sterolins: A Review of Their Immune-Modulating Properties, Alternative Medicine Review, vol. 4, No. 3, 1999, pp. 170-177.

Chinnah, A et al., Antigen dependent adjuvant activity of a polydispersed β-(1,4)-linked acetylated mannan (acemannan), Vaccine, vol. 10, No. 8, 1992, pp. 551-557.

Clamp, J R et al., Study of the Carbohydrate Content of Mucus Glycoproteins from Normal and Diseased Colons, Clinical Science, vol. 61 (1981), pp. 229-234.

Cuddihy, J et al., The Presence of Total Polysaccharides in Sugar Production and Methods for Reducing Their Negative Effects, Midland Research Laboratories, Inc.; date of publication, if any, unknown.

Davis, R, Polysaccharide: The Magic Bullet, Inside Aloe.

Djeraba, A et al., In vivo macrophage activation in chickens with Acemannan, a complex carbohydrate extracted from Aloe vera, International Journal of Immunopharmacology, vol. 22 (2000), pp. 365-372.

Dwek, R A, Glycobiology: The function of sugar in the IgG molecule, Anat., vol. 187 (1995), pp. 279-292.

Edwards, C A et al., Viscosity of food gums determined in vitro related to their hypoglycemic actions, Am J Clin Nutr vol. 46 (1987), pp. 72-77.

Ercan, N, Effects of Glucose, Galactose, and Lactose Ingestion on the Plasma Glucose and Insulin Response in Persons With Non-Insulin-Dependent Diabetes Mellitus, Metabolism, vol. 42, No. 12 (1993), pp. 1560-1567.

Feizi, T, Significance of carbohydrate components of cell surfaces, Autoimmunity and autoimmune disease, Wiley, Chichester (Ciba Foundation Symposium 129); (1987), pp. 43-58.

Fukuda, M et al., Molecular Glycobiology, Oxford University Press, pp. 1-52.

Ghoneum, M, Anti-HIV Activity in Vitro of MGN-3, an Activated Arabinoxylane from Rice Bran, Biochemical and Biophysical Research Communications, vol. 243 (1998), pp. 25-29.

Hakomori, S, Aberrant Glycosylation in Cancer Cell Membranes as Focused on Glycolipids: Overview and Perspectives, Cancer Research, vol. 45 (1985), pp. 2405-2414.

Hara, H et al., Ingestion of Guar Gum Hydrolysate, a Soluble Fiber, Increase Calcium Absorption in Totally Gastrectomized Rats, J. Nutr., vol. 129 (1999), pp. 39-45.

Haydu, C et al., Medical Attributes of Aloe vera—The Aloe Plant, Wilkes University (1997), pp. 1-8.

Ikegami, S et al., Viscous Indigestible Polysaccharides Reduce Accumulation of Pentachlorobenzene in Rats, J. Nutr., vol. 124 (1994), pp. 754-760.

Kahlon, J et al., Inhibition of AIDS virus replication by Acemannan in vitro, Mol. Biother., vol. 3 (1991), pp. 127-135.

Kelly, G., Larch Arabinogalactan: Clinical Relevance of a Novel Immune-Enhancing Polysaccharide, Altern Med Rev, vol. 4, No. 2 (1999), pp. 96-103.

Kidd, P, The Use of Mushroom Glucans and Proteoglycans in Cancer Treatment, Altern Med Rev, vol. 5, No. 1 (2000), pp. 4-27.

Knopp, R et al., Long-Term Blood Cholesterol-Lowering Effects of a Dietary Fiber Supplement, Am J Prev Med, vol. 17, No. 1 (1999), pp. 18-23.

Landin, K et al., Low blood pressure and blood glucose levels in Alzheimer's disease Evidence for a hypometablic disorder? J Intern Med, vol. 233 (1993), pp. 357-363.

Leclére, C et al., Role of viscous guar gums in lowering the glycemic response after a solid meal, Am J Clin Nutr, vol. 59 (1994), pp. 914-921.

Malhotra, R et al., Glycosylation changes of IgG associated with rheumatoic arthritis can activate complement via mannose-binding protein, Nature Medicine, vol. 1, No. 3 (1995), pp. 237-243.

Matsuda, K et al., Inhibitory Effects of Sialic Acid- or N-Acetylglucosamine-Specific Lectins on Histamine Release Induced by Compound 48/80, Bradykinin and Polyethylenimine in Rat Peritoneal Mast Cells, J. Pharmacol, vol. 64 (1994) pp. 1-8.

Olszewski, A et al., Plasma glucosamine and galactosamine in ischemic heart disease, Atherosclerosis, vol. 82 (1990), pp. 75-83.

Overton, P D et al., The effects of dietary sugar-beet fibre and guar gum on lipid metabolism in Wistar rats, British Journal of Nutrition, vol. 72 (1994), pp. 385-395.

Pelley, R, The Story of Aloe Polysaccharides, Inside Aloe, The International Aloe Science Council, Inc., Jan. 1997.

Peng, S Y et al., Decreased mortality of Norman Murine Sarcoma in mice treated with the immunomodulator, Acemannan™, Mol. Biother, vol. 3 (1991), pp. 79-87.

Petersen, M et al., Early Manifestation of the Carbohydrate-Deficient Glycoprotein Syndrome, J Pediatr, vol. 122 (1993), pp. 66-70.

Pugh, N et al., Characterization of Aloeride, a New High-Molecular-Weight Polysaccharide from Aloe Vera with Potent Immunostimulatory Activity, J Agnc Food Chem, vol. 49 (2001), pp. 1030-1034.

Qiu, Z et al., Modified Aloe barbadensis Polysaccharide with Immunoregulatory Activity, Planta Medica, vol. 66 (2000), pp. 152-156.

Ramelow, G et al., Uptake of metallic ions from aqueous solution by dried lichen biomass, Microbios, vol. 66 (1991), pp. 95-105.

Rest, R et al., Mannose Inhibits the Human Neutrophil Oxidative Burst, Journal of Leukocyte Biology, vol. 43 (1988), pp. 158-164.

Ryan, D et al., GG167 (4-Guanidino-2,4-Dideoxy-2,3-Dehydro-N-Acetylneuraminic Acid) Is a Potent Inhibitor of Influenza Virus in Ferrets, Antimicrobial Agents and Chemotherapy (1995), pp. 2583-2584.

Sampaio, A et al., A Galactose-Specific Lectin from the Red Marine Alga Ptilota Filicina, Phytochemistry, vol. 48, No. 5 (1998), pp. 765-769.

Sanchez, A et al., Role of sugars in human neutrophilic phagocytosis, Am J Clin Nutr, vol. 26 (1973), pp. 1180-1184.

Scott, J, Extracellular matrix, supramolecular organisation and shape, J Anat, vol. 187 (1995), pp. 259-269.

Fucoidan Research—Author unknown, Date of publication, if any, unknown.

Stone, K R, Glucosamine References, Arthritis & Glucasamine Resource Center (2004), pp. 1-10.

Teas, J, The Dietary Intake of Laminaria, a Brown Seaweed, and Breast Cancer Prevention, Nutrition and Cancer, vol. 4, No. 3 (1983), pp. 217-222.

Theodosakis, J et al., The Arthritis Cure, St. Martin's Press, NY, pp. 29-52; date of publication unkown.

Tizard, I, Aloe-derived carbohydrates reduce inflammation by blocking nutrophil emigration mediated by certain beta2 integrins, Abstract for presentation at IASC Scientific Seminar, Texas A&M University, College Station, Texas; date of publication unknown.

Tizard, I et al., The biological activities of mannans and related complex carbohydrates, Mol. Biother., vol. 1, No. 6 (1989), pp. 290-296.

Varki, A, Unusual modifications and variations of vertebrate oligosaccharides: are we missing the flowers for the trees? Glycobiology, vol. 6, No. 7 (1996), pp. 707-710.

Vlietinck, A J et al., Plant-Derived Leading Compounds for Chemotheraphy of Human Immunodeficiency Virus (HIV) Infection, Planta Medica, vol. 64 (1998), pp. 97-109.

Womble, D et al., Enhancement of Allo-Responsiveness of Human Lymphocytes by Acemannan (CARRISYN™), Int. J Immunopharmac., vol. 10, No. 8 (1988), pp. 967-974.

Womble, D et al., The Impact of Acemannan on the Generation and Function of Cytotoxic T-Lymphocytes, Immunopharmacology and Immunotoxicology, vol. 14, Nos. 1 and 2 (1992), pp. 63-77.

Zavoral, J et al., The hypolipidemic effect of locust bean gum food products in familial hypercholesterolemic adults and children, Am J Clin Nutr, vol. 38 (1983), pp. 285-294.

About Konnyaku, Author unknown, Date of publication, if any, unknown.

What's Glucomannan, Author unknown, Date of publication, if any, unknown.

Citkowitz, E., Developmental Biology (1972), 27: 494-503. "Analysis of the Isolated Hyaline Layer of Sea Urchin Embryos."

Balch, J.F. et al., "Prescription for Nutritional Healing", 2nd ed. (1997), Avery Publishing Group(USA), p. 7-8, 12-33 and 43-46.

Bartolome, A.P. et al., J. Agric. Food Chem.(1995), 43: 608-612, "Polysaccharides from the Cell Walls of Pineapple Fruit."

Alton, Gordon et al., "Direct Utilization of Mannose for Mammalian Glycoprotein Biosysnthesis", Glycobiology (1998) 8:3, 285-295.

Berger, Veronique et al., "Dietary Specific Sugars for Serum Protein Enzymatic Glycosylation in Man", Metabolism (1998) 47:12, 1499-1503.

Freeze, Hudson, "Disorders in Protein Glycosylation and Protein Therapy: Tip of an Iceberg?" The Journal of Pediatrics (Nov. 1998) 133:5, 593-600.

Gardiner, Tom et al., "Glyconutritionals: Consolidated Review of Potential Benefits", GlycoScience & Nutrition (Jul. 2001) 2:15, 1-15.

Martin, A. et al., "Availability of Specific Sugars for Glycoconjugate Biosynthesis: A Need for Further Investigations in Man", Biochimie (1998) 80:1, 75-86.

Rosalind Kornfeld and Stuart Kornfeld, "Assembly of Asparagine-Linked Oligosaccharides," Ann. Rev. Biochem., 1985, vol. 54, pp. 631-664.

Akira Kobata, "Structures and Functions of The Sugar Chains of Glycoproteins," Eur. J. Biochem, 1992, vol. 209, pp. 483-501.

Murray et al,. Harper's Biochemistry, Appleton & Lange, 1996, pp. 648-649.

J.H. Cummings et al., "A New Look at Dietary Carbohydrate: Chemistry, Physiology and Health," Eur. J. Clinical Nutrition, 1997, vol. 51, pp. 417-423.

Alan D. Elbein, "Inhibitors of the Biosynthesis and Processing of N-Linked Oligosaccharide Chains," Ann. Rev. Biochem., 1987, vol. 56, pp. 497-534.

Richard L. Jackson et al., "Glycosaminoglycans: Molecular Properties, Protein Interactions, and Role in Physiological Processes," Physiological Reviews, 1991, vol. 71, No. 2, pp. 481-539.

Arthur D. Lander, "Proteoglycans in the Nervous System," Current Opinion in Neurobiology, 1993, vol. 3, pp. 716-723.

Guido David, "Structural and Functional Diversity of the *Heparan Sulfate Proteoglycans*," Heparin and Related Polysaccharides, Plenum Press, 1992, pp. 69-78.

Geraldine McDowell and William A. Gahl, "Inherited Disorders of Glycoprotein Synthesis: Cell Biological Insights," Society for Experimental Biology and Medicine, 1997, vol. 215, pp. 145-157.

Leon Carayannopoulos and J. Donald Capra, "Immunoglobulins: Molecular Genetics," *Fundamental Immunology*, Third Edition, Raven Press, 1993, pp. 302-314.

Royston Jefferis et al., "Glycosylation Heterogeneity in Human IgG Subclass Proteins," Biochemical Society Transactions, 1998, vol. 16, pp. 340-341.

Mi-Hua Tao et al., "Studies of Aglycosylated Chimeric Mouse-Human IgG: Role of Carbohydrate in the Structure and Effector Functions Mediated by the Human IgG Constant Region," The Journal of Immunology, 1989, vol. 143, pp. 2595-2601.

Scot Hickman and Stuart Kornfeld, "Effect of Tunicamycin on IgM, IgA, and IgG Secretion By Mouse Plasmacytoma Cells," The Journal of Immunology, 1978, vol. 121, No. 3, pp. 990-996.

G. Doria et al., "Age-Dependent Variations of Antibody Avidity," Immunology, 1978, vol. 35, pp. 601-611.

Hironori Matsuda et al., "Proton Nuclear Magnetic Resonance Studies of the Structure of the Fc Fragment of Human Immunoglobulin GI: Comparisons of Native and Recombinant Proteins," Molecular Immunology, 1990, vol. 27, No. 6, pp. 571-579.

Norio Koide et al., Recognition of IgG by Fc Receptor and Complement: Effects of Glycosidase Digestion, Biochemical and Biophysical Research Communications, 1977, vol. 75, No. 4, pp. 838-844.

John Lund et al., "A Protein Structural Change in Aglycosylated IgG3 Correlates with Loss of huFcyR1 and huFcyR111 Binding And/Or Activation," Molecular Immunology, 1990, vol. 27, pp. 1145-1153.

Johann Deisenhofer et al., Crystallographic Structural Studies of a Human Fc Fragment, Hoppe-Seyler's Z. Physiol. Chem., 1976, vol. 357, pp. 1421-1434.

Jeffrey C. Edberg and Robert P. Kimberly, Cell Type-Specific Glycoforms of FcyR111a (CD 16), The American Association of Immunologists, 1997, pp. 3849-3857.

W. Ludo van der Pol and Jan G.J. van de Winkel, "IgG Receptor Polymorphisms: Risk Factors for Disease," Immunogenetics, 1998, vol. 48, pp. 222-232.

Kelly P. Kearse and Gerald W. Hart, "Topology of O-Linked N-Acetylglucosamine in Murine Lymphocytes," Archives of Biochemistry and Biophysics, Nov. 1991, vol. 290, No. 2, pp. 543-548.

M.R. Sairam, "Role of Carbohydrates in Glycoprotein Hormone Signal Transduction," The FASEB Journal, Jun. 1989, vol. 3, pp. 1915-1926.

C.A. Wilson et al., "Gonadotrophin glycosylation and function," Journal of Endocrinology, 1990, vol. 125, pp. 3-14.

M.R. Sairam et al., "Mechanism of Gonadotropin Action-Dissociation of Receptor Binding and Cellular Activation," Progress in Endocrinolgy, 1988, pp. 1025-1031.

Albert S. B. Edge et al., "Insulin Receptor Carbohydrate Units Contain Poly-*N*-Acetyllactosamine Chains," Endocrinology, 1990, vol. 127, No. 4, pp. 1887-1895.

Kim A. Heidenreich et al., "Structural Differences Between Insulin Receptors in the Brain and Peripheral Target Tissues," The Journal of Biological Chemistry, 1983, vol. 258, No. 14, pp. 8527-8530.

Elaine Collier et al., "Specific Glycosylation Site Mutations of the Insulin Receptor α Subunit Impair Intracellular Transport," Biochemistry, 1993, vol. 32, pp. 7818-7823.

Paola Briata et al., "Glucose Starvation and Glycosylation Inhibitors Reduce Insulin Receptor Gene Expression: Characterization and Potential Mechanism in Human Cells," Biochemical and Biophysical Research Communications, 1990, vol. 169, No. 2, pp. 397-405.

Stephen P. Jackson and Robert Tjian, "Purification and Analysis of RNA Polymerase II Transcription Factors by Using Wheat Germ Agglutinin Affinity Chromatography," Proc. Natl. Acad. Sci., USA, Mar. 1989, vol. 86, pp. 1781-1785.

Serge Lichtsteiner and Ueli Schibler, "A Glycosylated Liver-Specific Transcription Factor Stimulates Transcription of the Albumin Gene," Cell, 1989, vol. 57, pp. 1179-1187.

Rüdiger Göke et al., "Glycosylation of the GLP-1 Receptor Is a Prerequisite for Regular Receptor Function," Peptides, 1994, vol. 15, No. 4, pp. 675-681.

David A. Jans et al., "N-Glycosylation Plays a Role in Biosynthesis and Internalization of the Adenylate Cyclase Stimulating Vasopressin $V_2$-Receptor of LLC-$PK_1$ Renal Epithelial Cells: An Effect of Concanavalin A on Building and Expression," Archives of Biochemistry and Biophysics, 1992, vol. 294, No. 1, pp. 64-69.

Stuart Kornfeld, "Trafficking of Lysosomal Enzymes," The FASEB Journal, 1987, vol. 1, pp. 462-468.

Peter Walter et al., "Protein Translocation Across The Endoplasmic Reticulum," Cell, 1984, vol. 38, pp. 5-8.

Pauline M. Rudd et al., "Glycoforms Modify the Dynamic Stability and Functional Activity of an Enzyme," Biochemistry, 1994, vol. 33, pp. 17-22.

Pauline M. Rudd et al., "The Effects of Variable Glycosylation on the Functional Activities of Ribonuclease, Plasminogen and Tissue Plasminogen Activator," Biochimica et Biophysica Acta, 1995, vol. 1248, pp. 1-10.

C.P. Ponting et al., Plasminogen: A Structural Review,: Blood Coagulation and Fibrinolysis, 1992, vol. 3, pp. 605-614.

Mark W. C. Hatton et al., "Catabolism of Plasminogen Glycoforms I and II in Rabbits: Relationship to Plasminogen Synthesis by the Rabbit Liver In Vitro," Metabolism, 1994, vol. 43, No. 11, pp. 1430-1437.

Donald J. Davidson et al., "The Influence of the Nature of the Asparagine 289-linked Oligosaccharide on the Activation by Urokinase and Lysine Binding Properties of Natural and Recombinant Human Plasminogens," J. Clin. Invest., Jul. 1993, vol. 92, pp. 249-254.

Susan C. Howard et al., "Oligosaccharides at each Glycosylation Site Make Structure-Dependent Contributions to Biological Properties of Human Tissue Plasminogen Activator," Glycobiology, 1991, vol. 1, No. 4, pp. 411-417.

Eric Duverger et al., "Sugar-Dependent Nuclear Import of Glycoconjugates from the Cytosol," Experimental Cell Research, 1993, vol. 207, pp. 197-201.

Robert S. Haltiwanger et al., "O-Glycoslation of Nuclear and Cytoplasmic Proteins: Regulation Analogous to Phosphorylation?" Biochemical and Biophysical Research Communications, 1997, vol. 231, No. 2, pp. 237-242.

Frank I. Comer and Gerald W. Hart, "Dynamic Glycosylation of RNA Polymerase II," Molecular Biology of the Cell Abstracts, Abstract 2414, 1995, p. 415a.

Arup Chakraborty et al., "Regulation of eIF-2 α-Subunit Phosphorylation in Reticulocyte Lysate," Biochemistry, 1994, vol. 33, pp. 6700-6706.

David M. Kingsley et al., "Reversible Defects in O-Linked Glycosylation and LDL Receptor Expression in a UDP-Gal/UDP-GalNAc 4-Epimerase Deficient Mutant," Cell, Mar. 1986, vol. 44, pp. 749-759.

Takashi Yoshida et al., "Altered Function and Structure of Low-Density Lipoprotein Receptor in Compactin (ML236B)-Resistant Mutants of Chinese Hamster Cells," Biochimica et Biophysica Acta, 1987, vol. 921, pp. 575-586.

Karen Kozarsky et al., "Use of a Mutant Cell Line to Study the Kinetics and Function of O-Linked Glycosylation of Low Density Lipoprotein Receptors," Proc. Natl. Acad. Sci. USA, 1988, vol. 85, pp. 4335-4339.

Kermit L. Carraway et al., "Cell Surface Mucin-Type Glycoproteins and Mucin-Like Domains," Glycobiology, 1991, vol. 1, No. 2, pp. 131-138.

Christopher G. Tate and Randy D. Blakely, "The Effect of N-Linked Glycosylation on Activity of the Na+—and Cl- Dependent Serotonin Transporter Expressed Using Recombinant Baculovirus in Insect Cells," The Journal of Biological Chemistry, 1994, vol. 269, No. 42, pp. 26303-26310.

Malgorzata M. Zaleska and Maris Erecinska, "Involvement of Sialic Acid in High-Affinity Uptake of Dopamine by Synaptosomes from Rat Brain," Neuroscience Letters, 1987, vol. 82, pp. 107-112.

Jaak Jaeken et al., "The Carbohydrate-Deficient Glyoprotein Syndromes: Pre-Golgi and Golgi Disorders?" Glycobiology, 1993, vol. 3, No. 5, pp. 423-428.

K. Panneerselvam and Hudson H. Freeze, "Mannose Corrects Altered N-Glycosylation in Carbohydrate-Deficient Glycoprotein Syndrome Fibroblasts," J. Clin. Invest., Mar. 1996, vol. 97, No. 6, pp. 1478-1487.

Gordon Alton et al., "Oral Ingestion of Mannose Elevates Blood Mannose Levels: A First Step Toward Potential Therapy for Carbohydrate-Deficient Glycoprotein Syndrome Type 1," Biochemical and Molecular Medicine, 1997, vol. 60, pp. 127-133.

Ralf Niehues et al., "Carbohydrate-Deficient Glycoprotein Syndrome Type 1b," J. Clin. Invest., Apr. 1998, vol. 101, No. 7, pp. 1414-1420.

K. Panneerselvam et al., Abnormal Metabolism of Mannose in Families with Carbohydrate-Deficient Glycoprotein Syndrome Type 1, Biochemical and Molecular Medicine, 1997, vol. 61, pp. 161-167.

Taco W. Kuijpers, et al., "Antigen-Specific Immune Responsiveness and Lymphocyte Recruitment In Leukocyte Adhesion Deficiency Type II," International Immunology, 1997, vol. 9, No. 4, pp. 607-613.

A. Bond, et al., "The Relationship Between Exposed Galactose And N-Acetylglucosamine Residues On IgG in Rheumatoid Arthritis (RA), Juvenile Chronic Arthritis (JCA) and Sjögren's Syndrome (SS)," Clin. Exp. Immunol., 1996, vol. 105, pp. 99-103.

Rajneesh Malhotra, et al., "Glycosylation Changes of IgG Associated with Rheumatoid Arthritis Can Activate Complement Via the Mannose-Binding Protein," Nature Medicine, Mar. 1995, vol. 1, No. 3, pp. 237-243.

Katsuko Yamashita, et al., "Altered Glycosylation of Serum Transferrin of Patients with Hepatocellular Carcinoma," The Journal of Biological Chemistry, 1989, vol. 264, No. 5, pp. 2415-2423.

D. Biou, et al., "Microheterogeneity of the Carbohydrate Moiety of Human alpha 1-Acid Glycoprotein in Two Benign Liver Diseases: Alcoholic Cirrhosis and Acute Hepatitis," Clinica Chimica Acta, 1989, vol. 186, pp. 59-66.

Noriaki Kinoshita, et al., "α-Fetoprotein Antibody-Lectin Enzyme Immunoassay to Characterize Sugar Chains for the Study of Liver Diseases," Clinica Chimica Acta, 1989, vol. 179, pp. 143-152.

S. Thompson, et al., "Fucosylated forms of alpha-1 antitrypsin that predict unresponsiveness to chemotherapy in ovarian cancer," Br. J. Cancer, 1988, vol. 58, pp. 589-593.

S. Thompson and G. A. Turner, "Elevated Levels of Abnormally-Fucosylated Haptoglobins in Cancer Sera," Br. J. Cancer, 1987, vol. 56, pp. 605-610.

C. Sekine, et al., "The Reactivity of Alpha-1 Antitrypsin with *Lens Culinaris* Agglutinin and its Usefulness in the Diagnosis of Neoplastic Diseases of the Liver," Br. J. Cancer, 1987, vol. 56, pp. 371-375.

Jiri Mestecky, et al., "Defective Galactosylation and Clearance of IgA1 Molecules as a Possible Etiopathogenic Factor in IgA Nephropathy," IgA Nephropathy: The 25th Year, 1993, vol. 104, pp. 172-182.

Peter W. Gyves, et al., "Changes in the Sialylation and Sulfation of Secreted Thyrotropin in Congenital Hypothyroidism," Proc. Natl. Acad. Sci. USA, May 1990, vol. 87, pp. 3792-3796.

Barry P. Peters, et al., "O-Glycosylation of the α-Subunit Does Not Limit the Assembly of Chorionic Gonadotropin αβ Dimer in Human Malignant and Nonmalignant Trophoblast Cells," Endocrinology, 1989, vol. 124, No. 4, pp. 1602-1612.

James M. Roseman, et al., "The Effect of L-Focuse on Rat Mannary Tumor Growth, II *In Vitro* Studies" Journal of Surgical Oncology, 1971, vol. 3(1), pp. 79-88.

Daniel Wolfe, et al., "The Effect of L-Focuse on Rat Mannary Tumor Growth, I. *In Vivo* Studies" Journal of Surgical Onoclogy, 1971, vol. 3(1), pp. 73-77.

F. E. Rosato, et al., "Continuous Intravenous Fucose Treatment of Rat Mammary Tumor," Journal of Surgical Oncology, 1972, vol. 4, No. 2, pp. 94-101.

James L. Mullen, et al., "Continuous Intravenous Fucose Therapy in Rat Mammary Cancer II," Journal of Surgical Oncology, 1973, pp. 61-69.

Ryuichiro Nishimura, et al., "Free α Subunits of Glycoprotein Hormone with Dissimilar Carbohydrates Produced by Pathologically Different Carcinomas," Endocrinol. Japon., 1985, vol. 32 (4), pp. 463-472.

Kelly P. Kearse, et al., "Lymphocute Activation Induces Rapid Changes in Nuclear and Cytoplasmic Glycoproteins," Proc. Natl. Acad. Sci. USA, Mar. 1991, vol. 88, pp. 1701-1705.

Gordon D. Holt and Gerald W. Hart, "The Subcellular Distribution of Terminal N-Acetylglucosamine Moietes," 1986, vol. 261, No. 17, pp. 8049-8057.

Gerald W. Hart, "The Role of Asparagine-Linked Oligosaccharides in Cellular Recognition by Thymic Lymphocytes," Journal of Biological Chemistry, Jan. 1982, vol. 257, No. 1, pp. 151-158.

B. M. Gesner and V. Ginsburg, "Effect of Glycosidases on the Fate of Transfused Lymphocytes," Proceedings of the National Academy of Sciences, Sep. 1964, vol. 52, No. 3, pp. 750-755.

Deirdre R. Coombe and Christopher C. Rider, "Lymphocyte Homing Receptors Cloned—a Role for Anionic Polysaccharides in Lymphocyte Adhesion," Immunology Today, 1989, vol. 10, No. 9, pp. 289-291.

Timothy A. Springer, "Traffic Signals for Lymphocyte Recirculation and Leukocyte Emigration: The Multistep Paradigm," Cell, Jan. 1994, vol. 76, pp. 301-314.

Ghislain Opdenakker, et al., "Cells Regulate the Activities of Cytokines by Glycosylation," The FASEB Journal, Mar. 1995, vol. 9, pp. 456-457.

Andrew V. Muchmore and Jean M. Decker, "An Immunosuppressive 85-Kilodalton Glycoprotein Isolated From Human Pregnancy Urine is a High Affinity Ligand for Recombinant Interleukin 1α," The Journal of Biological Chemistry, 1986, vol. 261, No. 29, pp. 13404-13407.

Tristram G. Parslow and Dorothy F. Bainton, "Innate Immunity," *Medical Immunology*, Ninth Edition, 1997, pp. 25-42.

Philip H. Petra, et al., "Complete Enzymatic Deglycosylation of Native Sex Steroid-Binding Iprotein (SBP or SHBG) of Human and Rabbit Plasma: Effect on the Steroid-Binding Activity," Protein Science, 1991, vol. I, pp. 902-909.

David R. Joseph, et al., "The Role of Asparagine-Linked Oligosaccharides in the Subunit Structure, Steroid Binding, and Secretion of Androgen-Binding Protein," Molecular Endocrinology, 1992, pp. 1127-1134.

Cheryl A. Conover, "Glycosylation of Insulin-Like Growth Factor Binding Protein-3 (IGFBP-3) is not Required for Potentiation of IGF-I Action: Evidence for Processing of Cell-Bound IGFBP-3," Endocrinology, 1991, vol. 129, No. 6, pp. 3259-3268.

Haley E. Melikian, et al., "Inability to N-Glycosylate the Human Norepinophrine Transporter Reduces Protein Stability, Surface Trafficking, and Transport Activity but Not Ligand Recognition," Molecular Pharmacology, 1996, vol. 50, pp. 266-276.

Leon A. Bach, et al., "Human Insulin-Like Growth Factor Binding Protein-6 is O-Glycosylated," Biochemical and Biophysical Research Communications, 1992, vol. 186, No. 1, pp. 301-307.

L. R. Berghman, et al., "Disappearance Rate of Glycosylated and Non-Glycosylated Chicken Growth Hormone: Influence on Biological Activity," Comp. Biochem. Physiol., 1994, vol. 108C, No. 2, pp. 161-169.

Sue M. Firth and Robert C. Baxter, "The Role of Glycosylation in the Action of IGFBP-3," P rogress in Growth Factor Research, 1995, vol. 6, Nos. 2-4, pp. 223-229.

Patrick L. Storring, "Assaying Glycoprotein Hormones—the Influence of Glycosylation on Immunoreactivity," TBTech, Dec. 1992, vol. 10, pp. 427-432.

Jacques U. Baenziger, "Editorial: Glycosylation: To What End for the Glycoprotein Hormones?" Endocrinology, 1996, vol. 137, No. 5, pp. 1520-1522.

Bruce D. Weintraub, "TSH Immunoassay: Relationship Between Glycosylation & Bioactivity," Nucl. Med. Biol., 1990, vol. 17, No. 7, pp. 657-660.

John W. Cassels, et al., "Reduced Metabolic Clearance of Acidic Variants of Human Chriogonadotropin From Patients With Testicular Cancer," Cancer, 1989, vol. 64, pp. 2313-2318.

Wolfgang Jelkmann, "Erythropoietin: Structure, Control of Production, and Function," Physiological Reviews, Apr. 1992, vol. 72, No. 2, pp. 449-489.

Alfredo Ulloa-Aguirre, et al., "Immunological and Biological Potencies of the Different Molecular Species of Gonadotrophins," Human Reproduction, 1988, vol. 3, No. 4, pp. 491-501.

Eric D. Green and Jacques U. Baenziger, "Asparagine-Linked Oligosaccharides on Lutropin, Follitropin, and Thyrotropin," The Journal of Biological Chemistry, 1988, vol. 263, No. 1, pp. 36-44.

Eric D. Green, et al., "Differential processing of Asn-Linked Oligosaccharides on Pituitary Glycoprotein Hormones: Implications for Biologic Function," Molecular and Cellular Biochemistry, 1986, vol. 72, pp. 81-100.

L. Sl. Haro, et al., "Glycosylated Human Prolactin: Alterations in Glycosylation Pattern Modify Affinity for Lactogen Receptor and Values in Prolactin Radioimmunoassay," Journal of Clinical Endocrinology and Metablism, 1990, vol. 71, No. 2, pp. 379-383.

Masa-aki-Hattori, et al., "Sialic Acid Moiety is Responsible for the Charge Heterogeneity and the Biological Potency of Rat Lutropin," Biochemical and Biophysical Research Communications, Mar. 1985, vol. 127, No. 2, pp. 501-508.

Eylard V. Van Hall, et al., "Immunological and Biological Activity of HCG Following Progressive Desialytation," Feb. 1971, vol. 88, pp. 456-464.

Beldman, G et al., Biotechnology and Bioengineering (1987), 30(5): 668-71, Enzymatic hydrolysis of beer brewer's spent grain and the influence of pretreatments.

Beran, K. et al. Ceskoslov. mikrobiol. (1956), 1: 193-203. Saccharification of starch in potato mash with fungus amylolytic preparations.

Kato, T. et al., Jozo Kyokai Zasshi (1964), 59(5): 431-4. Soybean hull. 11. Hydrolyzate of soybean hull prepared by using cellulase. Abstract.

Remington, J.S. et al., Industrial Chemist and Chemical Manufacturer (1927), 3:155-7. Breakfast, invalid and infant food.

Communication from the U.S. Patent and Trademark Office dated Dec. 16, 2004 regarding U.S. Appl. No. 10/797,344, which is related to U.S. Appl. No. 10/797,760.

Communication from the U.S. Patent and Trademark Office dated Apr. 8, 2005 regarding U.S. Appl. No. 10/797,344, which is related to U.S. Appl. No. 10/797,760.

Communication from the U.S. Patent and Trademark Office dated Jul. 20, 2004 regarding U.S. Appl. No. 10/294,121, which is related to U.S. Appl. No. 10/797,760.

Communication from the U.S. Patent and Trademark Office dated Dec. 15, 2004 regarding U.S. Appl. No. 10/294,121, which is related to U.S. Appl. No. 10/797,760.

B. Thornton, et al.; *Analysis of the Sugar Specificity and Molecular Location of the B-Glucan-Binding Lectin Site of Complement Receptor Type 3 (CD11b/CD18)*; The Journal of Immunology, 1996, pp. 1235-1246.

L.S. Kind, et al.; *Enhanced Vascular Permeability Induced in Mice by Larch Arabinogalactan*; Immunology, 1970, 19, pp. 799-807.

J.N. Liu, et al.; *B Cell Stimulating Activity of Seaweed Extracts*; Int. J. Immunopharmac. vol. 19, No. 3, pp. 135-142, 1997.

C. Blondin, et al.; *Inhibition of Complement Activation by Natural Sulfated Polysaccharides (Fucans) From Brown Seaweed*; Molecular Immunology, vol. 31, No. 4, pp. 247-253, 1994.

E. Furusawa, et al.; *Antitumor Potential of Low-Dose Chemotherapy Manifested in Combination with Immunotherapy of Viva-Natural, a Dietary Seaweed Extract, on Lewis Lung Carcinoma*; Cancer Letters, 50 (1990), pp. 71-78.

G. Homann, et al.; *Mannan-Binding Protein and Complement Dependent Opsonization in Alcoholic Cirrhosis*; Liver 1995, 15, pp. 39-44.

A.C. Mann, et al.; *Monosaccharide Composition of Haptoglobin in Liver Diseases and Alcohol Abuse: Large Changes in Glycosylation Associated with Alcoholic Liver Disease*; Clinica Chimica Acta 227 (1994) pp. 69-78.

H. Stibler, et al.; *Evidence of a Reduced Sialic Acid Content in Serum Transferrin in Male Alcoholics*; Alcoholism: Clinical and Experimental Research, vol. 5, No. 4, Fall 1981, pp. 545-549.

F. Beauge, et al.; *Abnormal Fluidity and Surface Carbohydrate Content of the Erythrocyte Membrane in Alcoholic Patients*; Alcoholism: Clinical and Experimental Research, vol. 9, No. 4, Jul./Aug. 1985; pp. 322-326.

* cited by examiner

COMPOSITIONS OF PLANT CARBOHYDRATES AS DIETARY SUPPLEMENTS

CROSS-REFERENCE TO RELATED APPLICATIONS

This application is a continuation of application Ser. No. 09/242,215 filed Feb. 8, 1999 now U.S. Pat. No. 6,929,807, the entire disclosure of which is incorporated herein by reference, which is a U.S. national phase filing of International Application No. PCT/US97/13379 filed Aug. 4, 1997, which claims the priority of U.S. Provisional Application No. 60/022,467 filed Aug. 9, 1996, the entire disclosure of which is incorporated herein by reference, U.S. Provisional Application No. 60/030,317 filed Nov. 1, 1996, the entire disclosure of which is incorporated herein by reference, and U.S. Provisional Application No. 60/057,017 filed Jul. 24, 1997, the entire disclosure of which is incorporated herein by reference.

This application is related to prior filed application Ser. No. 10/294,121 filed Nov. 14, 2002, the entire disclosure of which is incorporated herein by reference, which is a divisional application of the above-identified application Ser. No. 09/242,215. This application is also related to a concurrently-filed application by McAnalley et al., which is entitled Compositions of Plant Carbohydrates as Dietary Supplements, the entire disclosure of which is incorporated herein by reference.

FIELD OF THE INVENTION

This invention pertains to the field of dietary supplements and nutritional support for promotion and maintenance of good health. More specifically, the invention relates to compositions of carbohydrates a dietary supplements that are essential for the production of correctly structured and, therefore, properly functioning glycoproteins.

DESCRIPTION OF THE PRIOR ART AND OTHER INFORMATION

The term mucus was first used in the 1700s. By 1805, Bostok realized that mucus was composed of protein that differed from albumin and gelatin. In 1865, Eichwald showed that mucins contained carbohydrate moieties. In 1877, Hoppe-Seyler discovered that mucins were high in sialic acid content. In 1882, Landwehr showed that plant gums, a type of mucin, contain more than one monosaccharide. With the advent of more modern methods, these monosaccharides were isolated and characterized. In 1888, Harmarsten showed that the saccharides in mucins were joined by a covalent bond; Harmarsten was the first to use the term "glykoproteide" (or glycoprotein in English). Fischer and Leuchs discovered high concentrations of mannose in mucus in 1902. Hayworth, in 1939, discovered N-acetylglucosamine and Bierry discovered galactose in 1930. Meyer discovered fucose in 1958 (Gottschalk, *Glycoproteins*, 1972).

Proteins were originally thought to be the primary "communication" molecules of the body. The biotechnology revolution began as an attempt to create new drugs based upon proteins which are made up of various combinations of amino acids. However, since amino acids can only bind to each other through an amide bond, the number of secondary configurations possible with proteins is limited. Indeed, only one secondary configuration is possible per dipeptide.

However, many more functions are performed by the body than can be accounted for by the number of molecular configurations possible with proteins. Several years ago a theoretical mathematician calculated the number of configurations possible with proteins and discovered that another mechanism, yet unknown, had to be responsible for performing most of the communication functions of the body. It is now known that this mechanism involves carbohydrates.

In contrast to the simpler proteins, more molecular configurations are possible with the more complex carbohydrate molecule, e.g., a hexose has six chiral centers each of which has two isomeric forms and each of which has a hydroxyl group as a binding site for other molecules. Thus, while only 24 oligopeptide configurations are possible with four amino acids, more than 100,000 different oligosaccharide configurations are possible with four sugars (Stryer et al., *Biochemistry* 1995; p 477).

Science has recently shown that glycoproteins play a key role in all cellular communication. Many of the cytokines, i.e. cellular messenger agents, do not function properly without an attached glycosyl moiety. The body hydrolyzes complex polysaccharides such as plant carbohydrates into various monosugars and restructures them into oligosaccharides that are then used by the body to build the glycoproteins required by cytokines for cellular communication and, thus, for good health.

With the advent of improved analytical techniques and more powerful computers, characterization of glycoproteins increased rapidly after the 1960s. By the mid 1980s, the mechanism of the orderly synthesis of glycoproteins in the endoplasmic reticulum and Golgi apparatus had been determined. The actual oligosaccharide conformations of many glycoproteins is now known.

Increasing interest in glycobiology has been precipitated by recent findings that cell surface carbohydrates are critically involved in cell adhesion and, thus, in cell-cell interaction. Specifically, three new mechanistic concepts have been discovered. First, structural studies in glycoproteins and glycolipids have revealed the existence of carbohydrates which are unique to certain cell types. This concept is crucial to understanding cell surface carbohydrates as cell-type specific recognition molecules.

A second concept was developed from new information regarding lectins, which have sugar-binding proteins. In the 1970s it was learned that glycoproteins were removed rapidly from the blood when their sialic acid, i.e. N-acetylneuraminic acid, containing branches were removed. Further studies revealed that this rapid clearance was caused by asialoglycoproteins binding to lectins that recognize terminal galactose. Once animal cells were known to have lectins, a large number of lectins were characterized, and a dedicated section in the amino acid sequence that is responsible for the carbohydrate recognition domain in the lectins was discovered. This discovery was critical to understanding carbohydrate-binding capability in cell-cell interactions. Thus, cellular communication was recognized at the molecular level.

The third concept resulted from studies regarding the isolation and characterization of the glycosyltransferases that form carbohydrates. These studies showed that carbohydrate moieties are usually built one by one, and each reaction is carried out by a glycosyltransferase that forms only a specific linkage. The advent of molecular biology in this field has enabled scientists to manipulate carbohydrate expression and study glycoprotein function.

Based on critical advances in this field, the most recent studies demonstrated that oligosaccharides uniquely present in leukocytes act as ligands for adhesive molecules in endothelia and platelets. When these adhesive molecules, known as selecting, were cloned, it was discovered that they contained carbohydrate recognition domains. Thus, studies on cell-type specific carbohydrates and animal lectins corroborated each other. Moreover, these studies were preceded by the findings that lymphocyte-endothelial interaction is dependent upon carbohydrates.

Given the above, research directed toward the synthesis of drugs that would correct malformation of glycoproteins on cell surfaces began. After the carbohydrate ligand sialyl-Le$^x$ was identified, pharmaceutical companies soon synthesized it for therapeutic purposes. This line of research has since become much easier because enzymatic synthesis of carbohydrates is now possible thanks to the availability of glycosyltransferases generated by cloned cDNAs (Fukuda et al., *Glycobiology*, 1994).

The synthesis of all proteins and glycoproteins is controlled by somatic genes embodied in the chromosomes of a cell. The coding information expressed in nucleic acids (DNA) controls all cellular functions, including general body defense, regeneration, remodeling and healing. Though DNA provides the blueprint, the cellular components cannot be built correctly without the required building blocks. As discussed above, cytokines are key components used for intracellular instruction to carry out the body's vital functions. However, many cytokines do not function properly without an attached glycosyl moiety.

Table 1 lists some of the known physiological functions served by glycoproteins. Table 2 lists some of the specific known functions that the oligosaccharide branches or chains of glycoproteins perform.

TABLE 1

Some known functions served by glycoproteins:

| Function | Glycoproteins |
|---|---|
| Structural molecule | Collagens |
| Lubricant and protective agent | Mucins |
| Transport molecule | Transferrin, ceruloplasmin |
| Immunologic molecule | Immunoglobulins, histocompatibility antigens |
| Hormone | Chorionic gonadotropin, thyroid- stimulating hormone (TSH) |
| Enzyme | Various, e.g., alkaline phosphatase |
| Cell attachment-recognition site | Various proteins involved in cell-cell (e.g., sperm-oocyte), virus-cell, bacterium-cell, and hormone-cell interactions |
| Interact with specific carbohydrates | Some lectins |

TABLE 2

Some known functions of the oligosaccharide chains of glycoproteins:

Modulate physicochemical properties, e.g., solubility, viscosity, charge, and protein denaturation
Protect against proteolysis from within and outside the cell
Affect proteolytic processing of precursor proteins to smaller products
Are involved in biologic activity, e.g., of human chorionic gonadotropin (hCG)
Affect insertion of protein into membranes, intracellular protein migration, and protein sorting and secretion
Affect embryonic development and differentiation
Affect metabolism
May affect sites of metastases selected by cancer cells In summary, various processes of the cell are regulated or affected by correctly structured and, therefore, properly functioning glycoproteins.

Despite the above discussed current scientific knowledge concerning the importance of glycoproteins to cell-cell communication and the importance of carbohydrates in the formation of glycoproteins, and despite the fact that diet is the source of a majority of carbohydrates, the fields of glycobiology and nutrition have never been adequately investigated together. Although current nutrition textbooks stress the importance of essential vitamins, minerals, proteins (amino acids) and fats in great detail, sugars are currently recognized only as a source of energy (Shils et al., 1994)—not as substances essential to glycoprotein production for good health. For example, Shils et al. disclose that the principal sources of dietary carbohydrates are: 1) maize, rice, wheat, and potato which yield starches comprising glucose; 2) sugar cane and beet sugar which yield fructose and glucose; and 3) milk which yields galactose and glucose (Shils et al., *Modern Nutrition in Health and Disease*, (1994)).

By way of contrast, Harper's Biochemistry (Murray et al., 1996) lists eight and Principles of Biochemistry, Vol II (Zubay et al., 1995) lists eleven monosaccharides commonly found in the oligosaccharide chains of cellular glycoproteins. Thus, of the approximate 200 monosaccharides found in nature, these eleven are believed to be important toward maintaining good health in mammals.

These eleven saccharides include galactose, glucose, mannose, N-acetylneuraminic acid, fucose, N-acetylgalactosamine, N-acetylglucosamine and xylose (Murray et al., *Harper's Biochemistry* 1996) as well as iduronic acid, arabinose and glucuronic acid, (Zubay et al., *Principles of Biochemistry*, Vol II, 1995). The structures of these carbohydrates are disclosed in Stryer's Biochemistry (Stryer, 1995) and the Merck Index, 12th Edition, 1996.

Recognizing this, scientists are currently trying, as yet with limited success, to synthetically attach glycosyl moieties to cytokines and other proteins. In fact, NIH has launched a project to develop methods to synthesize the glyco portion currently missing from their genetically engineered proteins. These synthetically produced cytokines have so far demonstrated disappointing results. Many challenges remain in this area. Scientists must first learn: 1) how to synthesize the glyco portion, 2) how to attach the glyco portion to the protein, and then 3) how to get the correct glycoproteins in the right concentrations to the right places in the body so as to facilitate good health.

For centuries, people of diverse cultures from around the world have utilized plants and herbs in the treatment of a wide variety of disorders in mammals. Specifically, formulations including poultices, teas, powders, pastes, extracts, plant or herb parts, plant or herbal extracts, lotions, creams, salves, troches, and others have been used. It is also now well recognized that much of the world's farm lands have been depleted of essential minerals required to sustain life, thus requiring the widespread use of vitamin, mineral and dietary supplements. A recent discovery concerns the importance of plant chemicals (phytochemicals) that are found in vine-ripened fruits and vegetables but are not found in those that are not vine-ripened. To provide these necessary, yet undefined, phytonutrients or phytonutritionals, as defined below, to the diet, some companies have begun supplying dietary supplements of freeze-dried, vine-ripened fruits and vegetables.

Nutritionists have developed hundreds of dietary supplement formulations in an effort to provide essential dietary components and facilitate and promote good health in mammals. However, fraudulent product claims regarding the treatment of physiological disorders are pervasive in the industry, and modern farming methods which focus on volume rather than nutritional value of crop production have led to crops having reduced dietary value that are missing essential dietary components.

Despite the extremely large number of dietary supplements available on store shelves today, the dietary needs of humans are still not being met. Many of such commercially available dietary supplements do not appear to provide any significant nutritional benefit. The present inventors believe such prior products suffer any one or more of the following disadvantages: a) they do not include the correct nutritional product(s); and b) their nutritional products are not well absorbed by a person taking them.

Thus, while scientists are beginning to recognize that other phytochemicals are required for good health, and others have previously recognized the utility of plants and herbs in the treatment of disorders, none of the known art suggests or discloses the invention as claimed herein. A need remains for non-pharmaceutical based dietary supplement formulations which provide essential saccharides that are the building blocks of glycoproteins and which promote good health in mammals.

SUMMARY OF THE INVENTION

It is an object of the present invention to provide a dietary supplement which promotes good health by providing to a mammal essential saccharides which are the building blocks of glycoproteins.

It has now been demonstrated herein by the present inventors that inclusion of these essential saccharides, as by supplementation of a diet with a dietary supplement containing the same, in the diets of mammals promotes good health. Although not intended to be limited to a particular mechanism of action, these essential saccharides are believed to be absorbed into the mammal's body and utilized in the formation of glycoproteins. By so providing these essential saccharides, the mammal's body does not have to spend energy unnecessarily catabolizing these essential saccharides and can therefore spend its energy providing for other physiological needs such as enhancement of the immune system to ward off, combat and/or ameliorate a wide range of physiological disorders.

Thus, the present invention overcomes the disadvantages and drawbacks of the prior art. One aspect of the present invention is directed to the use of various compositions of carbohydrates, i.e., glyconutritionals or glyconutrients, as dietary supplements which supplement a mammal's diet with sugars essential to glycoprotein and/or glycolipid production and thereby promote good health. In one embodiment, the present invention is directed to nutritional supplements including a defined amount of at least one of the eleven carbohydrates that are essential for the production of correctly structured and, therefore, properly functioning glycoproteins and/or glycolipids in a mammal. While some of these eleven sugars are readily available in common food sources, others are quite rare.

Accordingly, a first embodiment of the invention provides a dietary supplement for providing nutritional product saccharides which are essential components of glycoproteins in a mammal, said dietary supplement comprising a nutritionally effective amount of at least one saccharide, in monomeric, oligomeric or polymeric and derivatized or underivatized form, selected from the group consisting of: galactose, glucose, mannose, N-acetylneuraminic acid, fucose, N-acetylgalactosamine, N-acetylglucosamine; xylose, arabinose, glucuronic acid, galacturonic acid, iduronic acid, arabinogalactan, acetylated mannose, glucosamine and galactosamine.

In other embodiments of the invention, the dietary supplement comprises nutritionally effective amounts of at least two, at least three, at least four, at least five, at least six, at least seven, at least eight, at least nine, at least ten or at least eleven saccharides, in monomeric, oligomeric or polymeric and derivatized or underivatized forms selected from the above listed group. Since some of these saccharides have ionizable groups, the invention contemplates all known non-toxic salt forms thereof.

The monomeric, oligomeric or polymeric and derivatized or underivatized forms of these saccharides can be obtained from a wide variety of sources, such as for example, gum tragacanth, guar gum, grain flour, rice flour, sugar cane, beet sugar, potato, milk, agar, algin, locust bean gum, psyllium, karaya gum, seed gums, Larch tree extract, aloe vera extract, gum ghatti, starch, cellulose, degraded cellulose, fructose, high fructose corn syrup, pectin, chitin, acacia, gum arabic, alginic acid, carrageenan, dextran, xanthan gum, chondroitin sulfate, sucrose, acetylated polymannose, maltose, glucan, lentinan, mannan, levan, hemi-cellulose, inulin, fructan, and lactose.

Other embodiments of the invention can comprise phytochemicals or phytonutritionals derived from ripened and freeze-dried fruits and vegetables, dioscorea complex, herbal extracts, herbal body-toning agents, beta sitosterol, melatonin, soy lecithin, vitamins, or minerals.

In another embodiment of the present invention, the compositions include predigested forms of at least one of the eleven essential carbohydrates. This can include one or all of the following: 1) physical digestion such as shearing or treatment with ultrasound, 2) chemical digestion such as enzymatic digestion, and acid or base hydrolysis, and 3) biological digestion with microbes such as bacteria, fungi or molds.

In another aspect, the present invention is a dietary supplement for the modification of behavior in alcohol dependent mammals comprising nutritionally effective amounts of the natural and/or synthetic monomeric, oligomeric and/or polymeric forms of acetylated mannose, gum ghatti, gum tragacanth, glucosamine, corn starch and arabinogalactan. In a particular embodiment, the dietary supplement will reduce the craving for alcohol in an alcohol dependent mammal being administered the supplement. In another particular embodiment, the dietary supplement will improve the overall well being of the alcohol dependent mammal by reducing at least one of depression and anger or increasing at least one of cognition, energy and positive outlook.

In yet another aspect, the present invention is a dietary supplement for the reduction of undesired side-effects in mammals receiving biologically effective agents that cause said side-effects, said dietary supplement comprising nutritionally effective amounts of the natural and/or synthetic monomeric, oligomeric and/or polymeric forms of acetylated mannose, gum ghatti, gum tragacanth, glucosamine, corn starch and arabinogalactan. In a particular embodiment, the dietary supplement will reduce the undesired side-effects of central nervous system drugs. In a more particular embodiment, the dietary supplement will reduce the undesired side-effects of methylphenidate in a mammal suffering from attention-deficit hyperactivity disorder and receiving methylphenidate.

DETAILED DESCRIPTION

The body of a mammal hydrolyzes or metabolizes complex polysaccharides, such as plant carbohydrates, into various monosaccharides and subsequently forms oligosaccharides therefrom that are then used by the body to build the glycoproteins required by cytokines for cellular communication.

As used herein, the term "phytochemical" refers to plant synthesized molecules, found in food, or plant tissue in a complex organic matrix, which are minimally altered by processing from how they occur in nature. As used herein, the term "nutraceutical" refers to a non-toxic, nutrient of plant, mineral or animal origin, that has health promoting activity and that can be standardized and supplied as a dietary supplement to improve the nutritional quality of a balanced general diet. A nutraceutical is also a glyconutrient or phytonutrient.

As used herein, the terms "glyconutritional" or "glyconutrient" refer to complex carbohydrates or saccharides or simple sugars that are synthesized in nature and are necessary for the biochemical synthesis of various classes of communication and signal molecules that may be free in interstitial cellular fluids, active in cell to cell communication (i.e., cytokines, growth factors, etc.), or constitute the molecular configuration comprising foci of highly specific molecular activity of cell membranes (i.e., receptor sites, ion-transport channels, antigenic identification, and the like).

As used herein, the terms "phytonutritional" or "phytonutrient" refer to naturally synthesized molecules found only in plants that are produced to protect the plant's cells. Phytonutrients primarily have antioxidant, free-radical scavenger and vital micronutrient activity. These molecules, supplied through dietary supplementation, are found in mature plant tissues, and are most concentrated in seed coats and fruiting tissues surrounding the seed. In mammalian tissues, these molecules when supplied in the diet, are active in optimizing the biochemistry, immunology and physiology in the cellular micro-environment.

As used herein, the term "dioscorea complex" refers to an extract of dioscorea species (Mexican yam) providing a natural pre-cursor, dietary nutrient, diosgenin, a complex, six-ring, cyclic-carbon molecule that contains the molecular scaffold (perhydrocyclopentanophenanthrene) upon which mammalian adrenal and gonadal hormones are naturally synthesized. Providing this complex molecule in the diet can support optimal hormone balance, while maintaining normal physiological control mechanisms. This dietary supplement component has the potential to improve metabolic regulation of virtually every functioning cell in the body.

As used herein, the term "herbal extract" refers to phytochemicals that are produced in plant tissues and that can be extracted by water, polar, or petroleum solvents, and that have some degree of beneficial health or therapeutic activity. Most herbal agents can be toxic, especially when concentrated, but are generally safe when utilized in their more traditional manner in teas and poultices as a "folk medicinal for the treatment of disease and promotion of good health. As used herein, the term "herbal body-toning agent" refers to substances that have been observed by the inventors to reduce and reverse elastic tissue and collagen fiber damage caused by aging or sun-damage as evidenced by a restoration of skin turgor and elasticity which effectively reduces or eliminates wrinkles, sagging, hyperpigmentation and reversal of other undesirable elements of lost cosmetic appearance.

The carbohydrates included in the dietary supplement of the invention are available from a wide variety of natural and synthetic sources such as shrubs, trees, plants, yeasts, fungi, molds, gums, resins, starch and cellulose derivatives and natural mucin sources. Specifically, some of the natural sources include: (a) shrub or tree exudates which contain acacia, karaya, tragacanth, or ghatti; (b) marine gums which include agar, algin, or carrageenan; (c) seed gums which include guar, locust bean, or psyllium; (d) plant extracts which contain pectins or acetylated polymannose; (e) starch and cellulose derivatives such as hetastarch, carboxymethylcellulose, ethylcellulose, hydroxypropyl methylcellulose, methylcellulose, oxidized cellulose; and microbial gums which contain dextrans, xanthan. (Tyler et al., 1981) However, it should be recognized that the composition of the invention is not intended to be limited by the source from which the respective carbohydrates are obtained.

The saccharides of the invention can be found in nature as mono-, oligo- and/or polysaccharides. Thus, the compositions of the invention can contain the saccharides in their monomeric, oligomeric and/or polymeric forms. Table 3 below lists some of the known natural sources for the saccharides of the invention.

TABLE 3

Natural sources of saccharides.

| Source Carbohydrate | Corresponding Saccharide(s) |
| --- | --- |
| gum tragacanth | galacturonic acid, galactose, fucose, xylose, arabinose and rhamnose |
| guar gum | mannose and galactose (1:2 molar ratio) |
| rice or grain flour | glucose |
| LAREX B-1000 (Larch tree extract) | polyarabinogalactan |
| MANAPOL ® (aloe vera extract) | acetylated mannose based polymer |
| gum ghatti | arabinose, galactose, mannose, xylose, glucuronic acid (10:6:2:1:2 molar ratio) |
| starch | glucose |
| pectin | galacturonic acid |
| chondroitin sulfate | N-acetylgalactosamine |
| chitin | N-acetylglucosamine |
| acacia, gum arabic | arabinose, galactose, glucuronic acid |
| alginic acid | mannosyluronic acid, gulosyluronic acid |
| carrageenan | galactose, 3,6-anhycirogalactose |
| dextran | glucose |
| xanthan gum | glucose, mannose, glucuronic acid |

It is well recognized in the art that the saccharides listed above with their corresponding source carbohydrates are present in particular amounts in nature as exemplified by the indicated molar ratios for the saccharides in gum ghatti and guar gum. The relative amounts or ratios of saccharides in natural carbohydrates is readily determined using conventional extraction or analytical methods or can be obtained from literature sources commonly used in the art.

As used herein, the term "carbohydrate" is used interchangeably with the terms "saccharide", "polysaccharide", "oligosaccharide" and "sugar" the definitions of which are well known in the art of carbohydrate chemistry. Although the compositions of the invention are intended to include at least one of the eleven essential saccharides, it should be noted that the saccharides can be in the form of mono-, oligo- and/or polysaccharides, e.g. a composition containing gum tragacanth and guar gum will be considered as containing galacturonic acid, fucose, xylose, arabinose, rhamnose, mannose and galactose. Therefore, by controlling the amount of particular gums in a given dietary supplement, one can control the amount of the respective saccharides in said dietary supplement.

Although the present invention includes the above cited eleven essential saccharides, it should be noted that other saccharides, nutritional compounds or biologically active or inert compounds can be included in the dietary supplement of the invention. Such other nutritional compounds include any one or more of phytonutrients, dioscorea complex, plant extracts, herbal extracts, plant parts, herbal components, vitamins or minerals. These nutritional compounds can be added to the dietary supplement of the invention, or they can be provided separately to a mammal being administered said dietary supplement. For example, a person receiving the glyconutrient-containing dosage form of the invention can also receive a phytonutrient in either the same or a separate dosage form. Inert compounds can include flavors, fillers, lubricants, buffers, gels, binders, excipients, carriers and/or other such compounds that facilitate the formulation or administration of the inventive dietary supplement. All of the glyconutrient-containing dietary supplement compositions of the invention, even those containing additional compounds, agents or other substances, can be obtained directly from MANNATECH™. (Coppell, Tex.).

Dioscorea complex is available from Ayusherbs (Japan). When dioscorea complex is included in the dietary supplement of the invention, the ratio of dioscorea complex to total essential saccharide can range from about 0.0001/99.9999 to about 50/50 on a weight percent basis. In particular embodiments, the dioscorea complex to total essential saccharide ratio ranges from about 0.01–70/99.99–30 or about 10–40/90–60 or about 20/80.

Phytonutrients are available from a wide variety of manufacturing sources such as Cap-Tab (U.S.) or they can be added by freeze-drying and grinding ripe fruits and/or vegetables to form a powder which can then be added to or provided along with the dietary supplement of the invention. Such fruits and vegetables can be selected from all known fruits and vegetables but, in particular exemplary embodiments, include broccoli, brussel sprouts, cabbage, carrot, cauliflower, garlic, kale, onion, papaya, pineapple, tomato and turnip. These phytonutrients can be formulated in powder-containing caplet or capsule forms or in a base of gelatin and natural fruit fructose, optionally containing added flavors. When a phytonutrient is included in the dietary supplement of the invention, the ratio of total phytonutrient to total glyconutrient can range from about 0.001/99.999 to about 99.99/0.01 on a weight percent basis. As used herein, Phyto-1 refers to a dietary supplement comprising Glyco-1 (see Example 5), and freeze-dried raw fruits and vegetables. In particular embodiments, the phytonutrient to total glyconutrient ratio ranges from about 20–99/80–1 or about 50–95/50–5.

There are many plant and herbal extracts with suspected or demonstrated nutritional value which can promote good health and can be incorporated in or administered along with the dietary supplement of the invention. Such plant and herbal extracts can be obtained according to well known procedures for the extraction of substances, compounds or agents from plants or herbs. In particular embodiments, the dietary supplement of the present invention includes herbal or plant extracts of broccoli, brussel sprouts, cabbage, carrot, cauliflower, garlic, kale, onion, papaya, pineapple, tomato, asparagus, mushroom, parsnip, radish, and turnip. When a plant or herbal extract is included in the dietary supplement of the invention, the ratio of total extract (dry solids weight basis) to total glyconutrient can range from about 0.001–75/99.999–25 to about 10–90/90–10 on a weight percent basis.

Many different types of vitamins and minerals can be included in the dietary supplement of the invention. While a few vitamins and minerals of synthetic origin do possess nutritional value, particular embodiments of the dietary supplement herein contain nutritionally effective amounts of non-toxic vitamins and minerals obtained predominantly from natural sources. PROFILE™. is the tradename of a vitamin and mineral supplement used in the nutritional studies exemplified herein. This product, which can be obtained from MANNATECH™. (Coppell, Tex.), contains nutritionally effective amounts of the following vitamins and minerals: a) vitamins comprising A, B1, B12, B2, B6, beta carotene, bioflavanoids, biotin, C, choline, D, E, folic acid, inositol, K, niacinamide, para-aminobenzoic acid, and pantothenic acid; and b) minerals comprising boron, calcium, copper, GTF chromium, iodine, iron, magnesium, manganese, molybdenum, potassium, selenium, silicon, vanadium, and zinc. These vitamins and minerals may be provided in nutritionally acceptable non-toxic forms.

By "nutritionally effective amount" is meant that amount which will provide a beneficial nutritional effect or response in a mammal. For example, as nutritional response to vitamin- and mineral-containing dietary supplements varies from mammal to mammal, it should be understood that nutritionally effective amounts of said vitamins and minerals will vary, respectively. Thus, while one mammal may require a particular profile of vitamins and minerals present in defined amounts, another mammal may require the same particular profile of vitamins and minerals present in different defined amounts.

Other compounds, agents and nutrients can also be included in the dietary supplement of the invention, such as, for example, cellulose, calcium carbonate, kola nut, kola nut extract, country mallow, Atlantic kelp, cayenne pepper, silica, stearic acid, amino acids, glycine, lysine, glutamic acid, arginine, calcium carbonate, orchic substances, boron citrate, chromium picolinate, essential fibers, essential oils, essential botanicals, essential enteric ecology and flora growth promoters, essential fatty acids, live probiotic flora, proteins and enzymes.

The dietary supplement of the invention has been prepared and administered to mammals in powdered, reconstitutable powder, liquid-solid suspension, liquid, capsule, tablet, caplet, lotion and cream dosage forms. It should be readily obvious to one of ordinary skill in the science of formulations that the present dietary supplement can also be formulated appropriately for irrigation, ophthalmic, otic, rectal, sublingual, transdermal, buccal, vaginal, or dermal administration. Thus, other dosage forms such as chewable candy bar, concentrate, drops, elixir, emulsion, film, gel, granule, chewing gum, jelly, oil, paste, pastille, pellet, shampoo, rinse, soap, sponge, suppository, swab, syrup, chewable gelatin form, or chewable tablet can be used.

Due to varying diets among people, the dietary supplement of the invention can be administered in a wide range of dosages and formulated in a wide range of dosage unit strengths. For example, for those people who are missing from their diet nine of the eleven essential saccharides, a dietary supplement containing those nine saccharides in nutritionally effective amounts can be formulated. As well, for those people whose bioabsorption of essential saccharides is extremely efficient, a dietary supplement formulation containing reduced amounts of essential saccharides can be prepared.

It should be noted that the dosage of the dietary supplement can also vary according to a particular ailment or disorder that a mammal is suffering from when taking the supplement. For example, a person suffering from chronic fatigue syndrome, or fibromyalgia, will generally require a dose different than an alcoholic who is trying to discontinue alcohol consumption in order to obtain a nutritional benefit. An appropriate dose of the dietary supplement can be readily determined by monitoring patient response, i.e., general health, to particular doses of the supplement. As well, when another agent such as a phytonutrient, plant extract, herbal extract and/or dioscorea complex is being administered to a mammal along with the present glyconutritional dietary supplement, the appropriate doses of the supplement and each of the agents can be readily determined in a like fashion by monitoring patient response, i.e. general health, to particular doses of each.

It is contemplated by the invention that the dietary supplement can be administered simultaneously or sequentially in one or a combination of dosage forms. While it is possible and even likely that the present dietary supplement will provide an immediate overall health benefit, such benefit may take days, weeks or months to materialize. Nonetheless, the present glyconutritional dietary supplement will provide a beneficial nutritional response in a mammal consuming it.

It is also contemplated that the dietary supplement of the invention can be administered simultaneously or sequentially along with at least one of a phytonutrient, an herbal extract, a plant extract, and a dioscorea complex. Particular embodiments wherein the dietary supplement is administered simultaneously with at least one of a phytonutrient, an herbal extract, a plant extract, and a dioscorea complex are exemplified in the following examples.

For the examples herein, the dietary supplement of the invention was administered as a powder-containing capsule. When the dietary supplement included a phytonutrient, it was administered as a caplet or gelatin form. When the dietary supplement included a dioscorea complex, it was administered as either a capsule or caplet. When the dietary supplement included a phytonutrient, a dioscorea complex and an herbal extract, it was administered as a caplet.

According to the capsule or caplet size and ingredients used in a given study exemplified herein, the dietary supplement was administered initially as follows. The indicated doses are based upon #1 sized capsules and 1000–1200 mg caplets.

| SUPPLEMENT | DOSAGE |
| --- | --- |
| Glyco-1 | 2 capsules, 4x/day |
| Phyto-1 | 1 caplet, 4x/day |
| Glyco-1 with dioscorea complex | 1 caplet, 4x/day |
| PROFILE ™ | 1 tablet, 3x/day |

As the exemplified studies proceeded, the doses of the supplements were modified according to patient response to a prior dosing regimen. For example, if a patient's overall health was not improving at the initial dose, the respective dose for one or more of the supplements was modified. It should be noted that the actual doses ultimately given to each patient in a study varied greatly from patient to patient as nutritional response varied. Generally, the dietary supplement and each of the other supplements was administered in the range of about 1 to about 12 capsules (or caplets or tablets) per day.

It is well documented that biochemical individuality exists among mammals and results in a very wide range of drug or food required to obtain a desirable health promoting effect. (Williams, R.; in Nutrition Against Disease, 1971). The amount of the above nutraceuticals typically utilized initially as a dietary supplement is indicated for conditions of compromised health. Energy level, stiffness, pain, discomfort, restful sleep, recovery from fatigue, and emotional status are used as nutritional benefit markers in determining a mammal's nutritional response to the dietary supplement and in determining whether or not an increase in dose is warranted. A reduction of health complaints or a reduction or elimination of the above parameters is used as a guide for the reduction of glyconutrient intake. Complicating factors in regard to the amount of glyconutrients required for a benefit include the differing quantitative needs that individual have for nutrients, the differences being due to genetics, biochemical balance, disease state, altered physiology, prior and current general nutrition, individual choice and the nutrient content of food eaten by individuals. A desirable response or improvement in health is obtained when the missing nutrient or nutrients is/are adequately supplied by the present dietary supplement. The human body defends, repairs, regenerates, regulates, and heals itself through gene-control and nutrition provides the resources to accomplish these tasks. The inventive dietary supplement herein contain glyconutrients no longer commonly found in the urban/suburban food chain and thus supply a more optimal source of known and yet to be identified nutrients necessary for optimal biochemistry and physiology.

EXAMPLE 1

A suitable composition for a product according to the present invention is as follows: tragacanth gum (100 kg), a source of galacturonic acid, galactose, fucose, xylose, arabinose and rhamnose is charged into a stainless steel ribbon blender and guar gum (10 kg), a source of mannose and galactose, is charged into the stainless steel ribbon blender. The mixture of tragacanth gum and guar gum is mixed for five (5) minutes. Then 250 grams of Aerosil 380™ (silica gel) is added to the mixture as a flowing agent and 200 kilograms of rice flour, a source of glucose, is added as a gluten-free filler. The mixture is then agitated for fifteen (15) minutes. Finally, 100 grams of calcium stearate is added to the mixture as a lubricant and the mixture is agitated for an additional three (3) minutes to generate a bulk powder. The powder is then encapsulated into size 1 gelatin capsules at a fill weight of 250 mg using a Model 8 (Elanco) capsule filling machine.

EXAMPLE 2

Another suitable composition for a product according to the present invention is as follows: 25 kilograms each of galactose, glucose, mannose, N-acetylneuraminic acid, fucose, N-acetylgalactosamine, N-acetylglucosamine, and xylose available from Florida Food Products as well as Aldrich Chemical Company and Sigma Chemical is charged into a stainless steel ribbon blender and mixed for five (5) minutes. Then 250 grams of Aerosil 380™ (silica gel) is added to the mixture as a flowing agent and 200 kilograms of rice flour, a source of glucose, is added as a gluten-free filler. The mixture is then agitated for fifteen (15) minutes. Finally, 100 grams of calcium stearate is added to the mixture as a lubricant and the mixture is agitated for an additional three (3) minutes to generate a bulk powder. The powder is then encapsulated into size #1 gelatin capsules at a fill weight of 250 mg using a Model 8 (Elanco) capsule filling

EXAMPLE 3

Another suitable composition for a bulk product according to the present invention is as follows: This formulation can be prepared according to Example 2. The weight percentages indicated based upon the final weight of the composition.

| Percent by Weight | Ingredient | Approximate Density |
|---|---|---|
| 20 | Gum Tragacanth T/3 | 0.71 g/ml |
| 20 | Gum Ghatti No. 1 | 0.79 g/ml |
| 40 | arabinogalactan | 0.20 g/ml |
| 20 | MANAPOL ® | 0.12 g/ml |
|  | combined ingredients | 0.30 g/ml |

Gum tragacanth T/3 and Gum Ghatti No. 1 are both tree exudates that are available from AEP Colloids of Ballston Spa, N.Y. Arabinogalactan is obtained from the Larch tree and is available from North American Pharmacal of Norwalk, Conn. MANAPOL® is a freeze-dried aloe vera extract available from Carrington Laboratories (Irving, Tex.).

EXAMPLE 4

Standardization Assay

The following assay describes a method for standardization of concentrations of sugar covered by this patent.

Standards: All carbohydrate standards are available from Aldrich Chemical Company, Milwaukee, Wis.

Eluent: Deionized (DI) water having a resistance greater than or equal to about 17 MOhm.

Sample preparation: 2 ml of 2 N hydrofluoric acid are added to 10 mg of sample to be analyzed in a screw-top, TEFLON lined 10 ml test tube. The sample is then incubated at 120° C. for one hour to hydrolyze into monosaccharides. The excess reagent is removed under a stream of air and the sample resuspended in 1 ml of DI water.

HPLC Analysis: AOAC Official Methods of Analysis 977.20

EXAMPLE 5

The dietary supplement formulation of this example was prepared on large scale according to the above examples. This formulation, referred to as Glyco-1, includes the following ingredients in the amounts indicated. The weight percentage is based upon the weight of the final formulation containing all of the ingredients.

| Ingredient | Weight Percent |
|---|---|
| MANAPOL ® (aloe vera extract) | 10 |
| gum ghatti | 10 |
| gum tragacanth | 10 |
| glucosamine | 10 |
| corn starch | 12 |
| arabinogalactan | 48 |

This composition was formulated into topical and oral preparations as indicated above.

EXAMPLE 6

Reduction of Medicine Induced Side Effects in the Treatment of Attention-Deficit Hyperactivity Disorder Manual $4^{th}$ Ed. (DSM-IV) definitions for ADHD. One group consisted of five children whose parents had not placed them on methylphenidate (NO MED). The other 12 children in the study were receiving one of two different doses of methylphenidate: (a) six children received the normal prescribed dose (MED); and (b) six children received a reduced dose, i.e. below the normal prescribed dose (MED RED).

Assessment tools consisted of an ADHD rating scale for the DSM-IV symptoms; 18 items were rated on a scale of 0–3 for severity. Identical scales were constructed for the Oppositional Defiant Disorder (ODD) symptoms and the Conduct Disorder (CD) behaviors listed in DSM-IV. Both parents and teachers completed the above scales at each evaluation. In addition, parents completed a General Health Inventory for their children.

After all screening assessments were completed, all subjects had the glyconutritional product Glyco-1 added to their diets (1 capsule per 10 pounds of body weight for the first day and 1 capsule per 20 pounds of body weight for the remainder of the study). At week two, parent and teachers completed another rating series and the MED RED group had their medication reduced by half as per protocol. At week three, phytonutritionals (Phyto-1; 5 per day) were added to the dietary supplement procedure. The additional rating series were completed at weeks five and six.

The results indicated the Glyco-1 did not provide any further improvement in the ADHD symptomatology above that already obtained with the methylphenidate alone. However, a statistically significant reduction in the side-effects caused by the methylphenidate was obtained when Glyco-1 was administered to the subjects; therefore, an improvement in their overall general health was achieved.

EXAMPLE 7

Treatment of Alcoholics with Glyco-1

Glyco-1 capsules used in this study were prepared according to Example 6. The purpose of this study was to evaluate the effectiveness of dietary glyconutritional supplementation on the mood states and craving for alcohol in alcoholics. The study was conducted as follows.

Two groups of subjects were recruited from a local alcoholic support group in Little Rock, Ark.: three recovering alcoholics and two practicing alcoholics. Each met the Diagnostic and Statistical Manual $4^{th}$ Ed. (DSM-IV) criteria for alcohol dependency. In the recovering group, abstinence varied from 2.5 years to six years and 11 months. For both groups, years of alcohol abuse ranged from 15 to 30 years and ages ranged from 33 to 62.

Assessment tools consisted of a self-rating scale of craving for alcohol which was scored from 0 to 9 and the Profile of Mood States (POMS). The POMS 65 items were divided into five scales: Cognitive, Depression, Energy, Anger/Temper, and Positive Outlook. These assessments were completed prior to taking glyconutritionals and again at the end of the five-week study.

Glyconutritionals were added to each subject's diet: 1 capsule per 10 pounds of body weight for the first day and thereafter 1 capsule per 20 pounds of body weight for the duration of the trial. No other interventions were introduced.

Results indicated that the mean initial alcohol craving of the five subjects had decreased in a statistically significant manner. Likewise, the results also indicated statistically significant improvements in the all of the measured mood states.

EXAMPLE 8

Treatment of Various Disorders with Glyconutrients

The following table summarizes the results obtained when patients were administered Glyco-1 either alone or in combination with one or more of Phyto-1, Glyco-1 with dioscorea and PROFILE™. Each patient was administered an initial dose Glyco-1 and any one or more of the respective supplements in the dosages indicated as follows:

| SUPPLEMENT | DOSAGE |
| --- | --- |
| Glyco-1 (A) | 2 capsules, 4 x/day |
| Phyto-1 (B) | 1 caplet, 4 x/day |
| Glyco-1 with dioscorea complex (C) | 1 caplet, 4 x/day |
| PROFILE ™ (D) | 1 tablet, 3 x/day |

"E" indicates a topical hydrogel formulation comprising glyconutritionals

"F" indicates an oral dietary supplement comprising glyconutritionals and herbal extracts.

"E" indicates a topical hydrogel formulation comprising glyconutritionals

"F" indicates an oral dietary supplement comprising glyconutritionals and herbal extracts.

During each study, patient progress and nutritional or overall health response to administration of a given dietary supplement regimen was monitored. For those patients not responding well to initial doses, their dosing regimen was altered and their progress monitored again. It should be noted that in each of the cases, the Glyco-1 at an appropriate dose provided nutritionally effective amounts of the essential saccharide(s) necessary to promote good overall health in a given patient. That is, the glyconutrient-containing dietary supplement of the invention is not intended or professed to cure any of the disorders listed below. Rather, the dietary supplement provides a patient the necessary glyconutrients to permit a patient's own body to heal itself.

TABLE 4

Disorders treated by administration of glyconutrients alone or in combination with one or more of phytonutrients, dioscorea complex and vitamins and minerals.

| DISORDER | NUTRITIONAL PRODUCTS ADMINISTERED | TREATMENT RESULTS |
| --- | --- | --- |
| aging process or optimal health plan | A, B, C, D | decreased body fat; increased muscle mass and bone density; serum biochemistry altered to more healthy values |
| old stable strokes | A, B, C | restored sensory and muscular control |
| multiple sclerosis | A, B, C | restored sensory and muscular control |
| amyotrophic lateral sclerosis | A, B, C | restored sensory and muscular control |
| muscular dystrophy | A, B, C | restored sensory and muscular control |
| cerebral palsy | A, B, C | restored sensory and muscular control |
| macular degeneration | A, B, C | sight restorations |
| seizures | A, B, C | reduction or elimination of allergies and infections; coordination, learning, memory and appearance improvements |
| Down's Syndrome | A, B, C | reduction or elimination of allergies & infections; coordination, learning, memory and appearance improvements |
| systemic combined immune deficiency syndrome | A, B, C | antibody and T-cell function restoration |
| Tay-Sachs | A, B, C | restoration of lost functions |
| retinitis pigmentosis | A, B, C | sight restoration |
| color blindness | A, B, C | can see color |
| Huntington's chorea | A, B, C | restoration or improvement of lost functions |
| Alzheimer's | A, B, C | restoration or improvement of lost functions |
| Parkinson's | A, B, C | restoration or improvement of lost functions |
| inflammatory polyneuropathy | A, B, C | restoration or improvement of lost functions |
| Closed head traumatic syndromes | A, B, C | restoration or improvement of lost functions |
| spinal cord injury | A, B, C | restoration or improvement of lost functions |

TABLE 4-continued

Disorders treated by administration of glyconutrients alone or in combination with one or more of phytonutrients, dioscorea complex and vitamins and minerals.

| DISORDER | NUTRITIONAL PRODUCTS ADMINISTERED | TREATMENT RESULTS |
|---|---|---|
| ulcerative colitis | A, B, C | healed ulcers |
| Crohn's disease | A, B, C | healed ulcers |
| schizophrenia | A, B, C | improvements in functions |
| depression | A, B, C | improvements in functions |
| anxiety reactions | A, B, C | improvements in functions |
| compulsive disorders | A, B, C | improvements in functions |
| nervous tics | A, B, C | improvements in functions |
| restless leg syndrome | A, B, C | improvements in functions |
| Tourette's syndrome | A, B, C | improvements in functions |
| autism | A, B, C | improvements in functions |
| Wegener's granulomatosis | A, B, C | restoration of tissue |
| Lupus E. | A, B | healing of lesions |
| Rheumatoid arthritis | A, B | relief of symptoms |
| thyroiditis | A, B | normalization of antinuclear antibodies |
| myesthenia gravis | A, B | normalization of antinuclear antibodies |
| diabetes mellitus | A, B | normalization of glucose and Hgb AIC; restoration of renal functions; healing of ulcers, elimination of infection; elevated lipids normalize; reduced insulin and glycomeds |
| osteoporosis | A, B | reduced pain increased bone density |
| alcoholism | A | reduction in craving |
| cocaine | A | reduction in craving |
| atherosclerosis | A, B | reduced total cholesterol, LDL, and triglycerides and increased HDL; improved patency of vessels and arrhythmia |
| idiopathic myocarditis (presumed viral origin) | A, B | increased ejection function; restoration of heart size; increased Coxsackievirus antibody levels; and reversal of heart failure |
| rheumatoid arthritis | A, B | elimination of pain, stiffness, fever, and swelling; restoration of scope of motion, strength and endurance |
| degenerative arthritis | A, B | elimination of pain, stiffness, fever, and swelling; restoration of scope of motion, strength and endurance |
| traumatic arthritis | A, B | elimination of pain, stiffness, fever, and swelling; restoration of scope of motion, strength and endurance |
| juvenile arthritis | A, B | elimination of pain, stiffness, fever, and swelling; restoration of scope of motion, strength and endurance |
| asthma | A | elimination of shortness of breath and wheezing and improvement of pulmonary function |
| allergy-nasal, eyes, hay fever | A | elimination of itching, swelling, rash discomfort |
| silicon breast implant | A, B, C | reduction or elimination of symptoms |
| environmental toxin syndrome | A, B, C | reduction or elimination of symptoms |
| agent orange | A, B, C | reduction or elimination of symptoms |
| Gulf War syndrome | A, B, C | reduction or elimination of symptoms |
| Hepatitis B & C | A, C, D | normalization of liver enzymes and symptoms |
| influenza virus | A, C, D | prevention or amelioration; improvement of symptoms |

TABLE 4-continued

Disorders treated by administration of glyconutrients alone or in combination with one or more of phytonutrients, dioscorea complex and vitamins and minerals.

| DISORDER | NUTRITIONAL PRODUCTS ADMINISTERED | TREATMENT RESULTS |
|---|---|---|
| common cold | A, C, D | prevention or amelioration; improvement of symptoms |
| AIDS | A, C, D | elimination of symptoms; mRNA of HIV-1 is undetected; restored immune function |
| herpes | A, C, D | elimination of infestations |
| warts | A, C, D | elimination of infestations |
| human papillovirus | A, C, D | elimination of infestations |
| otitis media (chronic or persistent) | A, C, D | elimination of symptoms and need for antibiotics |
| leukemia | A, B, C, D | correction of altered chromosomes |
| lymphomas | A, B, C, D | normalization of tissue biopsies |
| sarcomas (astrocytomas) | A, B, C, D | normalization of tissue biopsies |
| adenocarcinomas such as breast, prostate, ovarian, gastrointestinal and lung | A, B, C, D | elimination of metastasis and shrinkage of mass to undetectable level |
| profound introversion and female impotence | A, B, C, D | restoration of psychological interest and physiological sexual function in the elderly |
| pain, ulcers and coldness of extremities in diabetes, raynauds, frost-bite, snake-bite and atherosclerosis | A, C, E | restoration to intact, painless extremity and microvascular circulation |
| sun damaged skin, age damaged skin, and radiation damaged skin | A, C, E | lessening of pigmentation, wrinkles, and lost elasticity and restoration of dermis and epidermis |
| athletic performance | C, F | increased strength and endurance, delayed fatigue, facilitation of recovery in young and aging athletes |

In summary, this invention pertains to the field of dietary supplements and nutritional support for promotion and maintenance of optimal good health. More specifically, the invention relates to compositions of carbohydrates as dietary supplements that are essential for the production of correctly structured and, therefore, properly functioning glycoproteins.

Science has recently shown that glycoproteins play a key role in all cellular communication. Many of the cytokines, i.e. cellular "words," do not function properly without an attached glycosyl moiety. The body hydrolyzes complex polysaccharides such as plant carbohydrates into various monosugars and restructures them into oligosaccharides that are then used by the body to build the glycoproteins required by cytokines for cellular communication and, thus, for good health.

This invention will correct the problem caused by modern diets consisting of highly refined foods, from which many essential ingredients have been eliminated during processing, specifically sugars needed for correctly structured and properly functioning glycoproteins.

The above is a detailed description of particular embodiments of the invention. Those of skill in the art should, in light of the present disclosure, appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

As used herein and unless otherwise indicated, the terms "a" and "an" are taken to mean "one", "at least one" or "one or more".

The invention claimed is:

1. A dietary supplement composition comprising:
   a nutritionally effective amount of isolated and purified acetylated mannose; and
   a nutritionally effective amount of at least five isolated and purified saccharides selected from: galactose, glucose, mannose, xylose, N-acetylneuraminic acid, fucose, N-acetylgalactosamine, N-acetylglucosamine, arabinose, glucuronic acid, galacturonic acid, iduronic acid and arabinogalactan.

2. The dietary supplement composition of claim 1, wherein the at least five isolated and purified saccharides are powdered.

3. The dietary supplement composition of claim 1, wherein the at least five isolated and purified saccharides are essential saccharides.

4. The dietary supplement composition of claim 1, wherein the at least five isolated and purified saccharides further comprise glucosamine and rhamnose.

5. The dietary supplement composition of claim 1, wherein the acetylated mannose and the at least five isolated and purified saccharides are dissolved in a liquid.

6. The dietary supplement composition of claim 1, wherein the acetylated mannose and the at least five isolated and purifed saccharides are encapulsated.

7. The dietary supplement composition of claim 1, wherein the acetylated mannose and the at least five isolated and purified saccharides are bioavailable.

8. The dietary supplement composition of claim 1, wherein the acetylated mannose is obtained from the group consisting of aloe vera and acetylated polymannose, and the at least five isolated and purified saccharides are obtained from the group consisting of gum tragacanth, guar gum, grain flour, rice flour, sugar cane, beet sugar, potato, milk, agar, algin, locust bean gum, psyllium, karaya gum, seed gums, Larch tree extract, gum ghatti, starch, cellulose, degraded cellulose, fructose, high fructose corn syrup, pectin, chitin, acacia, gum arabic, alginic acid, carrageenan, dextran, xanthan gum, chondroitin sulfate, sucrose, maltose, glucan, lentinan, mannan, levan, hemi-cellulose, inulin, fructan, and lactose.

9. The dietary supplement composition of claim 1, wherein the acetylated mannose and the at least five isolated and purified saccharides are provided in monomeric, oligomeric and/or polymeric forms.

* * * * *

UNITED STATES PATENT AND TRADEMARK OFFICE
CERTIFICATE OF CORRECTION

| | | |
|---|---|---|
| PATENT NO. | : 7,157,431 B2 | Page 1 of 1 |
| APPLICATION NO. | : 10/797760 | |
| DATED | : January 2, 2007 | |
| INVENTOR(S) | : McAnalley et al. | |

It is certified that error appears in the above-identified patent and that said Letters Patent is hereby corrected as shown below:

Column 8, line 44, change "3,6-anhycirogalactose" to -- 3,6-anhydrogalactose --.

Column 13, line 33, change "sugar" to -- sugars --.

Column 19, line 55, change "modem" to -- modern --.

Signed and Sealed this

Fifteenth Day of April, 2008

JON W. DUDAS
*Director of the United States Patent and Trademark Office*